(12) United States Patent
Letellier et al.

(10) Patent No.: US 8,710,101 B2
(45) Date of Patent: Apr. 29, 2014

(54) CO-CRYSTALS OF AGOMELATINE, A PROCESS FOR THERE PREPARATION AND PHARMACEUTICAL COMPOSITIONS CONTAINING THEM

(75) Inventors: Philippe Letellier, Orleans (FR); Michael Lynch, Saint Jean de la Ruelle (FR); Jean-Manuel Pean, Orleans (FR)

(73) Assignee: Les Laboratoires Servier, Suresnes Cedex (FR)

( * ) Notice: Subject to any disclaimer, the term of this patent is extended or adjusted under 35 U.S.C. 154(b) by 22 days.

(21) Appl. No.: 13/492,095

(22) Filed: Jun. 8, 2012

(65) Prior Publication Data

US 2012/0316245 A1   Dec. 13, 2012

(30) Foreign Application Priority Data

Jun. 9, 2011  (FR) ...................................... 11 01766
Aug. 25, 2011  (CN) .......................... 2011 1 0245039

(51) Int. Cl.
| A01N 37/18 | (2006.01) |
| A61K 31/16 | (2006.01) |
| C07C 233/00 | (2006.01) |
| C07C 235/00 | (2006.01) |
| C07C 237/00 | (2006.01) |
| C07C 239/00 | (2006.01) |

(52) U.S. Cl.
USPC .......................................... 514/630; 564/219

(58) Field of Classification Search
None
See application file for complete search history.

(56) References Cited

PUBLICATIONS

Vishweshwar et al. (Journal of Pharmaceutical Sciences, vol. 95, 499-516 (2006)).*
Daniel P. McNamara, et al, Pharmaceutical Research, vol. 23, No. 8, p. 1888-1897, Jul. 11, 2006.
French Preliminary Search Report for FR11/01766 of Nov. 16, 2011.
M.C. Etter, et al., Tetrahedron Letters, vol. 30, No. 28, p. 3617-3620, Jan. 1, 1989.
Martin Viertelhaus, et al, Crystal Growth & Design, vol. 9, No. 5, p. 2220-2228, May 6, 2009.
Nate Schulthesis, et al., Growth & Design, vol. 9, No. 6, p. 2950-2967, Jun. 3, 2009.
Remenar ,J.F. Journal of the American Chemical Society, vol. 125, p. 8456-8457, Jun. 1, 2003.
Sai-Li Zheng, et al, Crystal Growth & Design, vol. 11, p. 466-469, p. 471, FIG. 6, Feb. 2, 2011.
Trask A.V., et al., International Journal of Pharmaceutics, vol. 320, No. 1-2, p. 114-123, Aug. 31, 2006.

* cited by examiner

*Primary Examiner* — James D Anderson
*Assistant Examiner* — William Lee
(74) *Attorney, Agent, or Firm* — Hueschen and Sage

(57) ABSTRACT

New co-crystal of agomelatine composed of:
  agomelatine, or N-[2-(7-methoxy-1-naphthyl)ethyl]acetamide of formula (I)

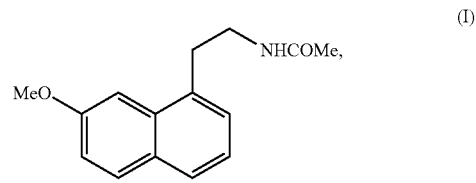

and
an organic acid.
Medicinal products containing the same which are useful in treating disorders of the melatoninergic system.

19 Claims, No Drawings

CO-CRYSTALS OF AGOMELATINE, A PROCESS FOR THERE PREPARATION AND PHARMACEUTICAL COMPOSITIONS CONTAINING THEM

The present invention relates to new co-crystals of agomelatine, or N-[2-(7-methoxy-1-naphthyl)ethyl]acetamide of formula (I):

to a process for their preparation and to pharmaceutical compositions containing them.

Agomelatine, or N-[2-(7-methoxy-1-naphthyl)ethyl]acetamide, has valuable pharmacological properties.

In fact, it has the double characteristic of being, on the one hand, an agonist of receptors of the melatoninergic system and, on the other hand, an antagonist of the $5-HT_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specification EP 0 447 285.

In view of the pharmaceutical value of this compound, a great deal of research work has been carried out, making it possible to isolate different polymorphic forms having various advantages, especially regarding purity, stability, reproducibility and formulation characteristics etc., allowing storage for an extended period without particular conditions regarding temperature, light, humidity or oxygen levels.

Furthermore, as with any active ingredient intended for administration to humans, it is very important to be able to control its dissolution rate so as to promote rapid or, on the contrary, slow diffusion.

The Applicant has now developed new co-crystals of agomelatine which make it possible to modify the dissolution rate of the active ingredient. The co-crystals according to the invention have a dissolution rate that is accelerated or delayed compared to the form available on the market which is described in patent specification EP 1 564 202 and marketed under the trade mark Valdoxan®. These new co-crystals having a modified dissolution profile accordingly make it possible to consider new formulations matched to the desired use.

A co-crystal is a crystal complex composed of at least two neutral molecules bound together in a crystal lattice by non-covalent interactions. The main difference between solvates and co-crystals is related to the physical state of the pure components: if one of the constituents is liquid at ambient temperature, the molecular complex is then a solvate; if all the components are solid at ambient temperature, the complex is then designated by the term "co-crystal". The major difference between a solvate and a co-crystal is the much greater stability of the co-crystal compared to the solvate. A co-crystal is characterised by the method by which it is obtained and by an ordered three-dimensional structure which is demonstrated, for example, by X-ray diffraction diagrams. It is not possible to know a priori whether two given constituents will be able to form a co-crystal having a particular three-dimensional structure or will simply give rise to a juxtaposition of the two powders. This particular three-dimensional structure bears a direct relationship to the dissolution rate of the entity thereby formed.

The invention relates more specifically to new co-crystals formed of agomelatine, on the one hand, and an organic acid, on the other hand. The co-crystals according to the invention comprise organic acids which are in a solid state at ambient temperature.

The organic acids according to the invention are linear or branched acids containing from 2 to 10 carbon atoms. They have one or more COOH acid function(s) and, more preferably, one, two or three acid function(s). They may also have, in addition to their acid function(s), one or more ketone function(s), one or more hydroxy function(s) and/or one or more unsaturated bond(s).

Among the organic acids that are constituents of the co-crystals according to the invention, there may be mentioned, by way of example, and without implying any limitation, para-hydroxybenzoic acid, citric acid, oxalic acid, gallic acid, maleic acid, malonic acid, glutaric acid, glycolic acid, ketoglutaric acid etc.

The proportion of organic acid used in relation to the agomelatine varies from 0.25 to 4 molar equivalents, preferably from 0.5 to 2 molar equivalents.

More especially, the invention relates to the following co-crystals: agomelatine/para-hydroxybenzoic acid (2/1) and (1/2); agomelatine/citric acid (1/1); agomelatine/oxalic acid (2/1); agomelatine/gallic acid (2/1); agomelatine/maleic acid (1/1); agomelatine/malonic acid (1/1); agomelatine/glutaric acid (1/1); agomelatine/glycolic acid (1/1); agomelatine/ketoglutaric acid (1/1).

The invention relates also to a process for obtaining co-crystals of agomelatine and organic acids, wherein:
  the two constituents are mixed in an organic solvent in the desired proportions (1 equivalent of agomelatine per 0.25 to 4 molar equivalents of organic acid);
  the solution obtained is stirred and optionally heated at a temperature not greater than the boiling point of the selected solvent;
  the mixture is cooled, with stirring, and the co-crystal precipitates naturally or precipitates after taking up in a second solvent;
  the precipitate obtained is filtered off and dried.

In the process according to the invention, the solvent used is preferably an alcohol such as, for example, methanol or tert-butanol; an ether such as, for example, diisopropyl ether or methyl tert-butyl ether; or an aromatic hydrocarbon such as, for example, toluene. When a second solvent is used in order to promote precipitation of the co-crystal, benzonitrile is advantageously selected.

An alternative process comprises co-grinding the two constituents of the co-crystal. The co-grinding is preferably carried out in a steel jar. A variant of this process comprises adding an organic solvent during the grinding; in this case, the co-crystal obtained is then dried. Among the solvents used, there may be mentioned, more especially, alcohols such as for example, ethanol or ethers such as, for example, diisopropyl ether.

The grinding is advantageously carried out using non-oxidisable balls. The grinding is carried out using vibrations, preferably vibrations having a frequency ranging from 20 to 30 Hz. The vibrations are applied for a period which may range from 15 minutes to 3 hours.

Another alternative process comprises mixing two solutions containing each of the constituents and rapidly freezing the mixture obtained at a very low temperature, and then at that same low temperature drying the co-crystal thereby obtained. The two constituents are advantageously mixed in an organic or aqueous-organic solvent. The freezing and drying are carried out preferably between −40° C. and −60° C., and more preferably at −40° C.

Another advantageous process according to the invention comprises mixing powders of agomelatine and of the acid in question in a mixer and then extruding by twin screw extrusion without a die in order to obtain a solid granular product directly at the extruder outlet. Preferably, the screw profile used is a high-shear profile, optionally using mixing elements making it possible to improve the surface contact between the two constituents. The L/D parameter of the screw may vary from 10 to 40 and the speed of rotation from 10 to 200 rpm. The temperature used varies from 40 to 100° C.

In the processes for preparation of the co-crystals according to the invention there may be used a compound of formula (I) that has been obtained by any process, especially by the process described in EP 1 564 202.

The co-crystals according to the invention exhibit properties that are highly valuable in terms of stability and dissolution—two essential parameters in the pharmaceutical industry. The dissolution of active ingredients is an important characteristic which may determine the rate of their adsorption in the human body. It is an important step in the release process, which has a major impact on the activity of a medicament. In fact, in order to cross biological membranes or in order to be absorbed, the active ingredient has to be dispersed in the molecular state in aqueous media (that is to say, dissolved) at the absorption site. The dissolution rate of the active ingredient is governed by its physico-chemical characteristics and also by the conditions of the absorption medium. It is accordingly important to have at one's disposal forms having a modified active ingredient dissolution rate, making it possible to obtain more, or less, rapid dissolution of the active ingredient matched to the desired use: a form having improved dissolution for use in immediate-release formulations, and a form having less rapid dissolution for use in retard or delayed-release formulations.

The co-crystals according to the invention meet this requirement, because it is possible to to modify the dissolution rate of agomelatine and to promote or reduce its dissolution by a factor of up to 2 relative to the form currently marketed in the pharmaceutical product Valdoxan®. More particularly, the co-crystals according to the invention make it possible to modify the active ingredient dissolution rate compared to the dissolution rate of the form currently marketed in the pharmaceutical product Valdoxan® by at least 25% under neutral (pH 6.8) or acid (0.01N HCl) conditions. It is accordingly possible to use the co-crystals according to the invention in developing immediate-release pharmaceutical forms in which the dissolution rate is improved relative to the form currently available on the market and also delayed-release forms in which the dissolution rate is retarded.

The pharmaceutical forms comprising the co-crystals according to the invention will be used for their activity in respect of the central nervous system and microcirculation, in the treatment of stress, sleep disorders, anxiety disorders and especially generalised anxiety disorder, obsessive-compulsive disorders, mood disorders and especially bipolar disorders, major depression, seasonal affective disorder, cardiovascular pathologies, pathologies of the digestive system, insomnia and fatigue due to jet-lag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and also in cerebral circulation disorders. In another field of activity, it will be possible to use the co-crystals according to the invention in sexual dysfunctions, as ovulation inhibitors and immunomodulators and in the treatment of cancers.

The co-crystals according to the invention will preferably be used in treatments for major depression, seasonal affective disorder, sleep disorders, anxiety disorders, mood disorders, cardiovascular pathologies, pathologies of the digestive system, insomnia and fatigue due to jet-lag, appetite disorders and obesity.

The invention relates also to pharmaceutical compositions comprising as active ingredient a co-crystal according to the invention together with one or more appropriate, inert, non-toxic excipients. Among the pharmaceutical compositions according to the invention there may be mentioned, more especially, those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and the age and weight of the patient. The dosage varies from 0.1 mg to 1 g of agomelatine per day in one or more administrations.

The Examples hereinbelow illustrate the invention but do not limit it in any way.

EXAMPLE 1

Co-Crystal of Agomelatine/Citric Acid (1/1)

Procedure A 3 g of N-[2-(7-methoxy-1-naphthyl)ethyl]acetamide and 2.6 g of citric acid are introduced into a 100-ml flask. 30 ml of MeOH are added and the solution is stirred for 20 hours at ambient temperature. After evaporation to dryness, the white gum obtained is taken up in 30 ml of benzonitrile added in portions of 3 ml. The suspension obtained is stirred until conversion of the gum into crystals is complete. After filtering, and washing with 20 ml of benzonitrile, the solid obtained is dried in vacuo at ambient temperature. It is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---:|---:|---:|
| 5.2156 | 16.94412 | 68.95 |
| 10.4436 | 8.47079 | 6.74 |
| 11.6034 | 7.62656 | 14.07 |
| 12.2434 | 7.2293 | 30.56 |
| 12.4588 | 7.10477 | 10.78 |
| 13.7638 | 6.43394 | 15.73 |
| 15.4174 | 5.74741 | 16.17 |
| 15.5925 | 5.68326 | 19.78 |
| 17.0703 | 5.19444 | 100 |
| 17.7473 | 4.99777 | 16.62 |
| 19.3834 | 4.57946 | 94.32 |
| 19.7762 | 4.48938 | 17.46 |
| 20.6894 | 4.29325 | 36.51 |

-continued

| 2-Theta (°) exp. | d (Å) exp. | Intensity (%) |
|---|---|---|
| 20.9759 | 4.23524 | 16.96 |
| 21.8985 | 4.05886 | 28.16 |
| 22.8106 | 3.89859 | 41.15 |
| 23.1664 | 3.83951 | 10.48 |
| 24.0776 | 3.69623 | 18.91 |
| 24.2435 | 3.6713 | 7.06 |
| 24.7742 | 3.59385 | 13.06 |
| 25.0152 | 3.55977 | 6.18 |
| 25.2672 | 3.52484 | 13.34 |
| 25.581 | 3.48231 | 5.37 |
| 26.3081 | 3.38769 | 16.92 |
| 26.5266 | 3.36028 | 17.15 |
| 27.0632 | 3.29486 | 6.91 |
| 27.2996 | 3.26687 | 30.63 |
| 27.8968 | 3.19827 | 8.39 |
| 28.7066 | 3.10986 | 7.1 |
| 29.6523 | 3.0128 | 9.86 |
| 31.4888 | 2.84116 | 17.44 |
| 34.4996 | 2.59979 | 5.96 |
| 35.0074 | 2.56324 | 5.71 |

Bragg's angles 2 theta (expressed in °±0.2) characteristic of the X-ray powder diffraction diagram: 5.21°, 12.24°, 17.07°, 19.38°, 20.69°, 21.90°, 22.81°, 27.30°.

Melting point: 126-129° C.

Procedure B 316.59 g of agomelatine and 250 g of citric acid monohydrate are mixed in a mixer of Turbula type for 10 minutes. The mixture is then extruded by twin screw extrusion without a die in order to obtain a solid granular product directly at the extruder outlet. A high-shear screw profile is used together with mixing elements in order to improve the surface contact between the two constituents. The L/D parameter of the screw used is 19. The rotation speed of the screws is 50 rpm for a feed rate measured at 300 g/h. The extrusion temperature is 55° C. The co-crystal obtained is characterised by its X-ray powder diffraction diagram, which is the same as that obtained by Procedure A.

EXAMPLE 2

Co-Crystal of Agomelatine/Gallic Acid (2/1)

A solution of 300.6 mg of N-[2-(7-methoxy-1-naphthyl)ethyl]acetamide in 15 ml of tert-butanol is slowly added to a solution of 106 mg of gallic acid in 35 ml of water in a 250-ml flask. The mixture is stirred for 10 minutes and then the solution is frozen to −40° C. and dried at that same temperature for 2 days in order to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 7.4888 | 11.8051 | 13.8 |
| 9.9347 | 8.90352 | 14.42 |
| 12.456 | 7.10638 | 9.11 |
| 12.7479 | 6.9443 | 14.08 |
| 14.0965 | 6.28286 | 5.63 |
| 14.4701 | 6.12146 | 20.24 |
| 16.7302 | 5.29926 | 14.01 |
| 16.829 | 5.26837 | 13.25 |
| 17.6782 | 5.01714 | 100 |
| 19.8178 | 4.48005 | 27.73 |
| 21.2441 | 4.18238 | 14.42 |
| 21.8521 | 4.06737 | 7.02 |
| 22.3357 | 3.98038 | 39.37 |
| 23.2889 | 3.81958 | 10.11 |
| 23.9313 | 3.71848 | 64.55 |
| 24.3882 | 3.64985 | 17.32 |
| 25.1812 | 3.53668 | 5.33 |
| 27.5931 | 3.23278 | 5.39 |
| 29.6861 | 3.00945 | 7.02 |
| 30.7722 | 2.90566 | 7.71 |

Bragg's angles 2 theta (expressed in °±0.2) characteristic of the X-ray powder diffraction diagram: 14.47°, 17.68°, 19.82°, 22.33°, 23.93°.

Melting point: 108-110° C.

EXAMPLE 3

Co-Crystal of Agomelatine/Maleic Acid (1/1)

1 g of N-[2-(7-methoxy-1-naphthyl)ethyl]acetamide and 482 mg of maleic acid are introduced into a 25-ml non-oxidisable jar. Two stainless steel balls of 12 mm diameter are added and the jar is closed. Vibrations with a frequency of 30 Hz are applied for 60 minutes to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 8.5443 | 10.34036 | 13.27 |
| 11.3006 | 7.82375 | 41.61 |
| 15.4031 | 5.74794 | 37.77 |
| 15.5752 | 5.68481 | 5.97 |
| 17.1135 | 5.17711 | 17.72 |
| 17.2840 | 5.12642 | 21.02 |
| 17.5446 | 5.05086 | 5.98 |
| 17.9818 | 4.92905 | 13.71 |
| 18.7041 | 4.74029 | 17.45 |
| 21.7442 | 4.08392 | 11.17 |
| 22.8692 | 3.88551 | 10.99 |
| 23.9084 | 3.71893 | 19.53 |
| 24.2950 | 3.66062 | 100 |
| 25.4494 | 3.49712 | 19.43 |
| 26.1055 | 3.4107 | 5.75 |
| 26.2070 | 3.39772 | 17.23 |
| 26.4841 | 3.36279 | 5.79 |
| 27.2254 | 3.27288 | 9.35 |
| 30.0238 | 2.9739 | 6.06 |
| 30.2591 | 2.95131 | 8.82 |

Bragg's angles 2 theta (expressed in °±0.2) characteristic of the X-ray powder diffraction diagram: 11.30°, 15.40°, 17.28°, 24.29°.

Melting point: 73-75° C.

EXAMPLE 4

Co-Crystal of Agomelatine/Malonic Acid (1/1)

A solution of 300 mg of N-[2-(7-methoxy-1-naphthyl)ethyl]acetamide in 15 ml of tert-butanol is slowly added to a solution of 129 mg of malonic acid in 35 ml of water in a 250-ml flask. The mixture is stirred for 30 minutes and then the solution is frozen to −40° C. and dried at that same temperature for 2 days in order to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 7.8661 | 11.23971 | 16.84 |
| 10.4713 | 8.44846 | 46.94 |
| 11.9502 | 7.406 | 45.62 |
| 12.7824 | 6.92563 | 9.99 |
| 14.7848 | 5.99187 | 21.65 |
| 15.3432 | 5.77504 | 19.95 |
| 16.0487 | 5.52273 | 100 |
| 16.7983 | 5.27793 | 11.99 |
| 16.9715 | 5.22445 | 13.9 |
| 17.1267 | 5.17745 | 9.19 |
| 21.0784 | 4.21489 | 9.77 |
| 22.3247 | 3.98233 | 23.32 |
| 24.0567 | 3.69939 | 6.29 |
| 24.5022 | 3.63313 | 56.82 |
| 25.0477 | 3.55523 | 23.07 |
| 25.2424 | 3.52825 | 40.38 |
| 25.7892 | 3.45467 | 10.44 |
| 26.7244 | 3.33585 | 7.17 |
| 27.3793 | 3.25753 | 20.44 |
| 27.9097 | 3.19682 | 26.63 |
| 29.4500 | 3.03304 | 10.41 |
| 34.0469 | 2.63332 | 5.16 |

Bragg's angles 2 theta (expressed in °±0.2) characteristic of the X-ray powder diffraction diagram: 10.47°, 11.95°, 14.78°, 16.05°, 22.32°, 24.50°, 25.05°, 25.24°, 27.38°, 27.91°.

Melting point: 67-68° C.

EXAMPLE 5

Co-Crystal of Agomelatine/Para-Hydroxybenzoic Acid (2/1)

1 g of N-[2-(7-methoxy-1-naphthyl)ethyl]acetamide and 283.8 mg of para-hydroxybenzoic acid are introduced into a 25-ml non-oxidisable jar. Two stainless steel balls of 12 mm diameter are added and the jar is closed. 200 μl of isopropyl ether are added. Vibrations with a frequency of 30 Hz are applied for 60 minutes to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 10.6835 | 8.28111 | 11.39 |
| 11.9471 | 7.40793 | 8.16 |
| 12.0698 | 7.33288 | 12.04 |
| 13.1596 | 6.72799 | 22.29 |
| 14.6189 | 6.05948 | 6.29 |
| 14.7754 | 5.99567 | 11.14 |
| 14.907 | 5.94301 | 43.41 |
| 15.1499 | 5.84827 | 14.08 |
| 16.7697 | 5.28686 | 7.17 |
| 17.08 | 5.19149 | 8.17 |
| 17.2378 | 5.14433 | 10.12 |
| 17.3731 | 5.10456 | 20.24 |
| 17.5783 | 5.04543 | 16.57 |
| 18.3905 | 4.82442 | 24.81 |
| 18.7565 | 4.73108 | 11.19 |
| 18.9282 | 4.68855 | 23.85 |
| 19.0366 | 4.6621 | 21.45 |
| 19.4137 | 4.57238 | 8.15 |
| 19.6471 | 4.5186 | 20.4 |
| 19.9637 | 4.44765 | 20.12 |
| 20.1044 | 4.41683 | 19.09 |
| 20.2539 | 4.38456 | 20.62 |
| 20.9205 | 4.24635 | 10.62 |
| 21.491 | 4.13489 | 100 |
| 21.7733 | 4.08191 | 91.9 |
| 22.2831 | 3.98966 | 7.75 |
| 23.7997 | 3.73875 | 12.32 |
| 23.9912 | 3.70935 | 8.36 |
| 24.2112 | 3.67614 | 6.78 |
| 24.6151 | 3.61672 | 17.26 |
| 24.9976 | 3.56224 | 22.13 |
| 26.5573 | 3.35646 | 4.98 |
| 26.7447 | 3.33337 | 5.85 |
| 27.5321 | 3.2398 | 12.36 |
| 29.4497 | 3.03306 | 12.87 |

Bragg's angles 2 theta (expressed in °±0.2) characteristic of the X-ray powder diffraction diagram: 13.16°, 14.91°, 17.37°, 18.39°, 18.93°, 19.04°, 19.65°, 19.96°, 20.25°, 21.49°, 25.00°.

Melting point: 93-95° C.

EXAMPLE 6

Co-Crystal of Agomelatine/Para-Hydroxybenzoic Acid (1/2)

1 g of N-[2-(7-methoxy-1-naphthyl)ethyl]acetamide and 1.14 g of para-hydroxybenzoic acid are introduced into a 25-ml non-oxidisable jar together with 250 μl of diisopropyl ether. Two stainless steel balls of 12 mm diameter are added and the jar is closed. Vibrations with a frequency of 30 Hz are applied for 120 minutes to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 6.9836 | 12.65784 | 17.63 |
| 8.4549 | 10.45823 | 6.16 |
| 9.4969 | 9.31293 | 34.61 |
| 12.2797 | 7.208 | 38.63 |
| 12.9651 | 6.82845 | 14.3 |
| 13.1503 | 6.7327 | 7.88 |
| 13.7866 | 6.42337 | 7.33 |
| 13.9951 | 6.32814 | 27.1 |
| 15.7604 | 5.62307 | 52.5 |
| 16.1791 | 5.4785 | 32.32 |
| 16.6241 | 5.33282 | 51.26 |
| 17.5572 | 5.05145 | 39.19 |
| 18.1485 | 4.8882 | 54.91 |

| 2-Theta (°) exp. | d (Å) exp. | Intensity (%) |
|---|---|---|
| 18.3819 | 4.82664 | 17.31 |
| 19.3253 | 4.5931 | 17.44 |
| 19.4415 | 4.56592 | 17.76 |
| 19.7593 | 4.49317 | 51.9 |
| 19.959 | 4.44867 | 42.09 |
| 21.0028 | 4.22989 | 45.52 |
| 21.2989 | 4.17175 | 20.42 |
| 22.0032 | 4.03979 | 60.83 |
| 22.6859 | 3.91973 | 11.33 |
| 22.9715 | 3.87164 | 20.19 |
| 23.5476 | 3.77821 | 39.55 |
| 23.7609 | 3.74477 | 93.42 |
| 24.4422 | 3.64191 | 32.21 |
| 25.3271 | 3.51664 | 19.07 |
| 25.5471 | 3.48685 | 14.62 |
| 26.0938 | 3.41502 | 100 |
| 26.8242 | 3.32367 | 21.88 |
| 26.9813 | 3.30467 | 16.4 |
| 27.9183 | 3.19586 | 6.85 |
| 28.4188 | 3.1407 | 27.49 |
| 28.7129 | 3.1092 | 30.36 |
| 29.276 | 3.05067 | 5.22 |
| 29.8536 | 2.99295 | 28.73 |
| 30.7825 | 2.90472 | 6.33 |
| 34.5702 | 2.59464 | 5.06 |

Bragg's angles 2 theta (expressed in °±0.2) characteristic of the X-ray powder diffraction diagram: 9.50°, 12.28°, 14.00°, 15.76°, 16.18°, 16.62°, 17.56°, 18.15°, 19.96°, 21.00°, 21.30°, 22.00°, 22.97°, 23.55°, 23.76°, 24.44°, 26.09°, 26.82°, 28.42°, 28.71°, 29.85°.

Melting point: 116-118° C.

EXAMPLE 7

Co-Crystal of Agomelatine/Oxalic Acid (2/1)

1 g of N-[2-(7-methoxy-1-naphthyl)ethyl]acetamide and 185.5 mg of oxalic acid are introduced into a 25-ml non-oxidisable jar. Two stainless steel balls of 12 mm diameter are added and the jar is closed. Vibrations with a frequency of 30 Hz are applied for 15 minutes to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 8.7632 | 10.09092 | 8.8 |
| 12.4791 | 7.09329 | 100 |
| 13.8057 | 6.41451 | 28.18 |
| 14.0254 | 6.31452 | 63.44 |
| 14.2244 | 6.22663 | 31.66 |
| 15.302 | 5.79047 | 61.34 |
| 15.4283 | 5.74335 | 27.34 |
| 17.6112 | 5.03608 | 83.89 |
| 17.8165 | 4.97852 | 55.54 |
| 19.6373 | 4.52082 | 57.35 |
| 19.7701 | 4.49075 | 45.05 |
| 21.533 | 4.12692 | 37.04 |
| 21.7182 | 4.08876 | 64.35 |
| 21.7902 | 4.07878 | 58.69 |
| 21.9725 | 4.04535 | 62.54 |
| 24.2928 | 3.66397 | 16.29 |
| 24.9548 | 3.56825 | 55.55 |
| 25.3868 | 3.50851 | 45.81 |
| 26.4367 | 3.3715 | 11.92 |
| 26.7285 | 3.33536 | 6.99 |
| 27.3623 | 3.25682 | 24.66 |
| 27.4684 | 3.24718 | 36.5 |
| 27.8038 | 3.20876 | 12.84 |
| 29.2866 | 3.04959 | 26.14 |
| 29.768 | 3.00136 | 26.04 |
| 30.8738 | 2.89633 | 5.28 |
| 31.2434 | 2.86291 | 8.55 |
| 31.853 | 2.8095 | 5.8 |

Bragg's angles 2 theta (expressed in °±0.2) characteristic of the X-ray powder diffraction diagram: 12.48°, 13.80°, 14.02°, 14.22°, 15.30°, 15.43°, 17.61°, 17.82°, 19.64°, 19.77°, 21.53°, 21.72°, 21.79°, 21.97°, 24.95°, 25.39°, 27.36°, 27.47°, 29.29°, 29.77°.

Melting point: 112.5-114.5° C.

EXAMPLE 8

Co-Crystal of Agomelatine/Glutaric Acid (1/1)

1 g of N-[2-(7-methoxy-1-naphthyl)ethyl]acetamide and 555 mg of glutaric acid are introduced into a 25-ml non-oxidisable jar. Two stainless steel balls of 12 mm diameter are added and the jar is closed. Vibrations with a frequency of 30 Hz are applied for 60 minutes to yield the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 9.5919 | 9.22091 | 22.85 |
| 10.3486 | 8.5483 | 28.18 |
| 11.9618 | 7.39882 | 23.63 |
| 13.0927 | 6.76218 | 8.08 |
| 13.7395 | 6.44526 | 5.45 |
| 14.7283 | 6.0147 | 8.81 |
| 16.4376 | 5.39291 | 13.05 |
| 16.9847 | 5.2204 | 10.58 |
| 17.493 | 5.06987 | 10.05 |
| 17.6723 | 5.01881 | 6.83 |
| 18.6123 | 4.76741 | 17.35 |
| 18.9534 | 4.68238 | 15.44 |
| 19.9041 | 4.46083 | 16.48 |
| 20.5662 | 4.31869 | 20.46 |
| 21.6468 | 4.10548 | 38.05 |
| 21.9751 | 4.04488 | 5.01 |
| 22.0881 | 4.02444 | 5.94 |
| 23.3395 | 3.81143 | 100 |
| 23.7133 | 3.75217 | 6.65 |
| 24.0288 | 3.70362 | 5.71 |
| 24.6109 | 3.61733 | 5.25 |
| 25.0027 | 3.56152 | 6.82 |
| 25.863 | 3.44497 | 8.04 |
| 27.6684 | 3.22415 | 17.51 |
| 29.1279 | 3.06584 | 4.97 |

Bragg's angles 2 theta (expressed in °±0.2) characteristic of the X-ray powder diffraction diagram: 9.59°, 10.35°, 11.96°, 20.57°, 21.65°, 23.34°.

Melting point: 74-75° C.

EXAMPLE 9

Co-Crystal of Agomelatine/Ketoglutaric Acid (1/1)

1 g of N-[2-(7-methoxy-1-naphthyl)ethyl]acetamide and 600 mg of ketoglutaric acid are introduced into a 25-ml non-oxidisable jar together with 500 µl of ethanol. Two stainless steel balls of 12 mm diameter are added and the jar is closed. Vibrations with a frequency of 30 Hz are applied for 15 minutes to yield, after drying overnight at 40° C., the title product, which is characterised by its melting point and by the following X-ray powder diffraction diagram, measured using a Panalytical Xpert Pro MPD diffractometer (copper anti-cathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 5.2391 | 16.86816 | 18.25 |
| 6.1796 | 14.30283 | 7.39 |
| 9.6513 | 9.16426 | 12.13 |
| 10.4827 | 8.43926 | 8.6 |
| 14.2638 | 6.20954 | 5 |
| 15.3616 | 5.76815 | 45.63 |
| 16.3452 | 5.41872 | 43.96 |
| 16.5381 | 5.35593 | 59.36 |
| 17.0478 | 5.20123 | 6.44 |
| 18.3191 | 4.84305 | 8.1 |
| 19.2396 | 4.61337 | 21.8 |
| 20.5617 | 4.31961 | 7.64 |
| 21.036 | 4.22329 | 12.12 |
| 21.3726 | 4.15752 | 7.66 |
| 23.57 | 3.77466 | 36.07 |
| 23.9026 | 3.7229 | 24.64 |
| 24.4145 | 3.64597 | 100 |
| 26.4474 | 3.37016 | 6.58 |
| 29.1314 | 3.06548 | 6.73 |
| 37.1969 | 2.41723 | 5.98 |

Bragg's angles 2 theta (expressed in °±0.2) characteristic of the X-ray powder diffraction diagram: 15.36°, 16.34°, 16.54°, 19.24°, 23.57°, 23.90°, 24.41°.

Melting point: 94-96° C.

EXAMPLE 10

Co-Crystal of Agomelatine/Glycolic Acid (1/1)

1 g of N-[2-(7-methoxy-1-naphthyl)ethyl]acetamide and 319 mg of glycolic acid are introduced into a 25-ml non-oxidisable jar. Two stainless steel balls of 12 mm diameter are added and the jar is closed. Vibrations with a frequency of 30 Hz are applied for 15 minutes to yield, after drying overnight at 40° C., the title product, which is characterised by its melting point and by the following X-ray powder diffraction diagram, measured using a Panalytical Xpert Pro MPD diffractometer (copper anticathode) and expressed in terms of interplanar distance d, Bragg's angle 2 theta (expressed in °±0.2), and relative intensity (expressed as a percentage relative to the most intense line):

| 2-Theta (°) exp. | d (Å) exp. | Intensity (%) |
|---|---|---|
| 10.2906 | 8.59638 | 45.79 |
| 13.9365 | 6.35459 | 5.32 |
| 14.1139 | 6.27513 | 31.57 |
| 14.2265 | 6.22572 | 24.57 |
| 14.3625 | 6.16708 | 11.84 |
| 17.9846 | 4.93237 | 90.49 |
| 18.617 | 4.76622 | 10.66 |
| 18.8288 | 4.71308 | 89.79 |
| 19.19 | 4.62519 | 9.61 |
| 19.5137 | 4.54918 | 30.43 |
| 19.941 | 4.45266 | 6.52 |
| 20.6101 | 4.30959 | 66.27 |
| 20.9906 | 4.23232 | 8.23 |
| 22.8209 | 3.89685 | 6.31 |
| 23.6248 | 3.76604 | 5.61 |
| 23.9623 | 3.71375 | 26.41 |
| 24.2171 | 3.67524 | 17.2 |
| 24.3906 | 3.64949 | 100 |
| 26.4458 | 3.37037 | 27.5 |
| 28.1154 | 3.1739 | 29.75 |
| 28.4808 | 3.134 | 5.71 |
| 28.6849 | 3.11217 | 6.41 |
| 28.9288 | 3.08648 | 5.75 |
| 29.518 | 3.02621 | 29.2 |
| 32.2458 | 2.77386 | 14.35 |

Bragg's angles 2 theta (expressed in °±0.2) characteristic of the X-ray powder diffraction diagram: 10.29°, 14.11°, 14.23°, 17.98°, 18.83°, 19.51°, 20.61°, 23.96°, 24.39°, 26.44°, 28.11°, 29.52°.

Melting point: 75-77° C.

EXAMPLE 11

Measurement of the Dissolution Rate of the Co-Crystals

Measurement of the dissolution rates of the co-crystals obtained is carried out with aid of a µDISS analytical apparatus (pION) in an acidic and a neutral medium at 37° C. using a stirring speed of 700 rpm. The results obtained are collated in the following tables and are expressed as percentage increases in the dissolution rate of the co-crystal compared to the dissolution rate obtained for agomelatine of form II contained in the marketed Valdoxan® form:

$$\% = \frac{\text{(Dissolution rate of co-crystal)} - \text{(Dissolution rate of Valdoxan)}}{\text{(Dissolution rate of Valdoxan)}} \times 100$$

|  | 0.01N HCl | pH 6.8 buffer |
|---|---|---|
| Compound of Example 1 | +25% | +70% |
| Compound of Example 2 | +37% | +29% |
| Compound of Example 5 | +97% | +89% |
| Compound of Example 6 | +19% | +46% |
| Compound of Example 7 | +1.5% | +33% |

The results obtained show an increase in the dissolution rate of the co-crystals which ranges from 33% to 97% under at least one of the two, acid or neutral, conditions tested.

|  | 0.01N HCl | pH 6.8 buffer |
| --- | --- | --- |
| Compound of Example 3 | −26% | −4% |
| Compound of Example 4 | −55% | −21% |
| Compound of Example 8 | −42% | −29% |
| Compound of Example 9 | −47% | −32% |
| Compound of Example 10 | −30% | −30% |

The results obtained show a reduction in the dissolution rate of the co-crystals which ranges from 26% to 55% under at least one of the two, acid or neutral, conditions tested.

EXAMPLE 12

Accelerated-Release Pharmaceutical Composition

Formula for the preparation of 1000 tablets each containing 25 mg of agomelatine:

| | |
| --- | --- |
| Compound of Example 5 | 50 g |
| Lactose monohydrate | 115 g |
| Magnesium stearate | 2 g |
| Maize starch | 33 g |
| Maltodextrins | 15 g |
| Anhydrous colloidal silica | 1 g |
| Pregelatinised maize starch, Type A | 9 g |

EXAMPLE 13

Retarded-Release Pharmaceutical Composition

Formula for the preparation of 1000 tablets each containing 25 mg of active ingredient:

| | |
| --- | --- |
| Compound of Example 9 | 50 g |
| Lactose monohydrate | 100 g |
| Magnesium stearate | 2 g |
| Povidone | 12 g |
| Anhydrous colloidal silica | 1 g |
| Hypromellose | 85 g |

The invention claimed is:
1. A co-crystal of agomelatine, comprising:
agomelatine, or N-[2-(7-methoxy-1-naphthyl)ethyl]acetamide of formula (I)

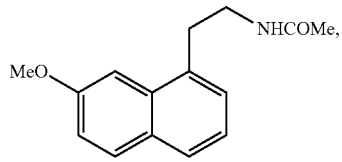

and
an organic acid which is in a solid state at ambient temperature, wherein the co-crystal is selected from:
N-[2-(7-methoxy-1-naphthyl)ethyl]acetamide/para-hydroxybenzoic acid (2/1);
N-[2-(7-methoxy-1-naphthyl)ethyl]acetamide/para-hydroxybenzoic acid (1/2);
N-[2-(7-methoxy-1-napthyl)ethyl]acetamide/citric acid (1/1);
N-[2-(7-methoxy-1-napthyl)ethyl]acetamide/oxalic acid (2/1);
N-[2-(7-methoxy-1-napthyl)ethyl]acetamide/gallic acid (2/1);
N-[2-(7-methoxy-1-naphthyl)ethyl]acetamide/maleic acid (1/1);
N-[2-(7-methoxy-1-naphthyl)ethyl]acetamide/malonic acid (1/1);
N-[2-(7-methoxy-1-naphthyl)ethyl]acetamide/glutaric acid (1/1);
N-[2-(7-methoxy-1-naphthyl)ethyl]acetamide/glycolic acid (1/1); and
N-[2-(7-methoxy-1-naphthyl)ethyl]acetamide/ketoglutaric acid (1/1).

2. The co-crystal according to claim 1, which is N-[2-(7-methoxy-1-naphthyl)ethyl]acetamide/para-hydroxybenzoic acid (2/1), having the following X-ray powder diffraction diagram (Bragg's angles 2 theta (expressed in °±0.2)): 13.16°, 14.91°, 17.37°, 18.39°, 18.93°, 19.04°, 19.65°, 19.96°, 20.25°, 21.49°, 25.00°.

3. The co-crystal according claim 1, which is N-[2-(7-methoxy-1-naphthyl)ethyl]acetamide/para-hydroxybenzoic acid (1/2), having the following X-ray powder diffraction diagram (Bragg's angles 2 theta (expressed in °±0.2)); 9.50°, 12.28°, 14.00°, 15.76°, 16.18°, 16.62°, 17.56°, 18.15°, 19.96°, 21.00°, 21.30°, 22.00°, 22.97°, 23.55°, 23.76°, 24.44°, 26.09°, 26.82°, 28.42°, 28.71°, 29.85°.

4. The co-crystal according to claim 1, which is N-[2-(7-methoxy-1-naphthyl)ethyl]acetamide/citric acid (1/1), having the following X-ray powder diffraction diagram (Bragg angles 2 theta (expressed in °±0.2)): 5.21°, 12.24°, 17.07°, 19.38°, 20.69°, 21.90°, 22.81°, 27.30°.

5. The co-crystal according to claim 1, which is N-[2-(7-methoxy-1-naphthyl)ethyl]acetamide/oxalic acid (2/1), having the following X-ray powder diffraction diagram (Bragg's angles 2 theta (expressed in °±0.2)): 12.48°, 13.80°, 14.02°, 14.22°, 15.30°, 15.43°, 17.61°, 17.82°, 19.64°, 19.77°, 21.53°, 21.72°, 21.79°, 21.97°, 24.95°, 25.39°, 27.36°, 27.47°, 29.29°, 29.77°.

6. The co-crystal according to claim 1, which is N-[2-(7-methoxy-1-naphthyl)ethyl]acetamide/gallic acid (2/1), having the following X-ray powder diffraction diagram (Bragg's angles 2 theta (expressed in °±0.2)): 14.47°, 1768°, 19.82°, 22.33°, 23.93°.

7. The co-crystal according to claim 1, which is N-[2-(7-methoxy-1-naphthyl)ethyl]acetamide/maleic acid (1/1), having the following X-ray powder diffraction diagram (Bragg's angles 2 theta (expressed in °±0.2)): 11.30°, 15.40°, 17.28°, 24.29°.

8. The co-crystal according to claim 1, which is N-[2-(7-methoxy-1-naphthyl)ethyl]acetamide/malonic acid (1/1), having the following X-ray powder diffraction diagram (Bragg's angles 2 theta (expressed in °±0.2)): 10.47°, 11.95°, 14.78°, 16.05°, 22.32°, 24.50°, 25.05°, 25.24°, 27.38°, 27.91°.

9. The co-crystal according to claim 1, which is N-[2-(7-methoxy-1-naphthyl)ethyl]acetamide/glutaric acid (1/1), having the following X-ray powder diffraction diagram (Bragg's angles 2 theta (expressed in °±0.2)): 9.59°, 10.35°, 11.96°, 20.57°, 21.65°, 23.34°.

10. The co-crystal according to claim 1, which is N-[2-(7-methoxy-1-naphthyl)ethyl]acetamide/glycolic acid (1/1), having the following X-ray powder diffraction diagram (Bragg's angles 2 theta (expressed in °±0.2)): 14.11°, 14.23°, 17.98°, 18.83°, 19.51°, 20.61°, 23.96°, 24.39°, 26.44°, 28.11°, 29.52°.

11. The co-crystal according to claim 1, which is N-[2-(7-methoxy-1-naphthyl)ethyl]acetamide/ketoglutaric acid (1/1), having the following X-ray powder diffraction diagram (Bragg's angles 2 theta (expressed in °±0.2)): 15.36°, 16.34°, 16.54°, 19.24°, 23.57°, 23.90°, 24.41<.

12. A process for obtaining the co-crystal according to claim 1, comprising:
   mixing the agomelatine and the organic acid in an organic solvent in the desired proportions (1 equivalent of agomelatine per 0.25 to 4 molar equivalents of organic acid);
   stirring the solution so obtained and optionally heating the solution at a temperature not greater than the boiling point of the selected solvent;
   cooling the mixture, with stirring, and to precipitate the co-crystal naturally or adding a second solvent to precipitate the co-crystal;
   filtering and drying the precipitate so obtained.

13. A process for the preparation of the co-crystal according to claim 1, wherein the agomelatine and the organic acid are co-ground.

14. A process for the preparation of the co-crystal according to claim 1, wherein the agomelatine and the organic acid are mixed in an organic or aqueous-organic solvent and then frozen and dried at a very low temperature.

15. A process for the preparation of the co-crystal according to claim 1, wherein powders of agomelatine and of the organic acid are mixed in a mixer and then the mixture is extruded by twin screw extrusion without a die in order to obtain a solid granular product directly at the extruder outlet.

16. A pharmaceutical composition comprising as active ingredient a co-crystal according to claim 1, in combination with one or more pharmaceutically acceptable, inert, non-toxic carriers.

17. A method of treating disorders of the melatoninergic system, in a subject in need thereof, comprising administration of an effective amount of the co-crystal according to claim 1.

18. A method of treating a condition selected from stress, sleep disorders, anxiety disorders, obsessive-compulsive disorders, mood disorders, major depression, seasonal affective disorder, cardiovascular pathologies, pathologies of the digestive system, insomnia and fatigue due to jet-lag, schizophrenia, panic attacks, melancholia, appetite disorders, obesity, insomnia, pain, psychotic disorders, epilepsy, diabetes, Parkinson's disease, senile dementia, disorders associated with normal or pathological aging, migraine, memory loss, Alzheimer's disease, cerebral circulation disorders, sexual dysfunctions, conditions requiring an ovulation inhibitor, conditions requiring an immunomodulator, and cancer, in a subject in need thereof, comprising administration of an effective amount of the co-crystal according to claim 1.

19. The method of claim 18, wherein the condition is selected from generalised anxiety disorders and bipolar disorders.

* * * * *

UNITED STATES PATENT AND TRADEMARK OFFICE
CERTIFICATE OF CORRECTION

PATENT NO. : 8,710,101 B2  
APPLICATION NO. : 13/492095  
DATED : April 29, 2014  
INVENTOR(S) : Philippe Letellier, Michael Lynch and Jean-Manuel Pean It is certified that error appears in the above-identified patent and that said Letters Patent is hereby corrected as shown below:

In the Claims

Claim 6, Column 14, Line 45: "1768°" should be --17.68°--.

Claim 10, Column 15, Line 1: "14.11°'" should be --10.29°, 14.11°--.

Claim 11, Column 15, Line 8: "24.41<" should be --24.41°--.

Signed and Sealed this  
Twelfth Day of August, 2014

Michelle K. Lee  
*Deputy Director of the United States Patent and Trademark Office*